United States Patent [19]

Skötsch et al.

[11] Patent Number: 4,598,083
[45] Date of Patent: Jul. 1, 1986

[54] ALKYLTHIOCINNAMIC ACID NITRILES FOR THE CONTROL OF HARMFUL ORGANISMS

[75] Inventors: Carlo Skötsch; Hartmut Joppien; Ernst A. Pieroh, all of Berlin, Fed. Rep. of Germany

[73] Assignee: Schering Aktiengesellschaft, Berlin and Bergkamen, Fed. Rep. of Germany

[21] Appl. No.: 623,133

[22] Filed: Jun. 18, 1984

[30] Foreign Application Priority Data

Jun. 16, 1983 [DE] Fed. Rep. of Germany ....... 3322281

[51] Int. Cl.$^4$ ...................... A01N 43/40; A01N 37/34
[52] U.S. Cl. .................................... 514/357; 558/401; 558/373; 546/330; 549/75; 514/438; 514/520; 514/525
[58] Field of Search .......... 260/465 F, 465 G, 465 K; 546/330; 549/75; 424/304; 514/357, 438, 520, 525

[56] References Cited

U.S. PATENT DOCUMENTS 3,828,091  8/1974  Strong ........................... 260/465 G
3,852,276 12/1974  Cresswell et al. ............. 260/465 K Primary Examiner—Dolph H. Torrence
Attorney, Agent, or Firm—Michael J. Striker

[57] ABSTRACT

A composition is disclosed for the control of harmful organisms, containing at least one α-alkylthiocinnamic acid nitrile of the formula

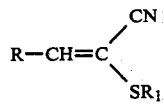

I in which R is an if necessary, one or more times, the same or differently, substituted by halogen, $C_1$-$C_4$-alkyl, $C_1$-$C_4$-alkoxy, $C_1$-$C_4$-alkylthio or trifluoromethyl, aromatic hydrocarbon and $R_1$ is a straight-chain $C_1$-$C_4$-alkyl or cyanoethyl, as well as a process for the production of these compounds and a method for the control of said harmful organisms.

2 Claims, No Drawings

ALKYLTHIOCINNAMIC ACID NITRILES FOR THE CONTROL OF HARMFUL ORGANISMS

BACKGROUND OF THE INVENTION

The invention concerns α-alkylthiocinnamic acid nitriles, processes for the production of these compounds as well as compositions containing the same and useful for the control of harmful organisms.

3-Alkylthio-2-aryl-acrylonitrile with herbicidal effectiveness are known, for example from U.S. Pat. No. 3,828,091. However, these compounds are not suitable for the control of harmful organisms.

It is therefore an object of the present invention to make available a composition which is effective in the control of such harmful organisms.

SUMMARY OF THE INVENTION

This object is attained according to the present invention by means of a composition that is characterized by a content of at least one α-alkylthiocinnamic acid nitrile of the general formula

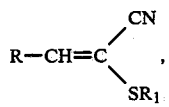    I in which
R is an aromatic hydrocarbon which may be substituted with at least one substituent selected from the group consisting of halogen, ($C_1$-$C_4$) - alkyl, ($C_1$-$C_4$) - alkoxy, ($C_1$-$C_4$) - alkylthio and trifluoromethyl and $R_1$ is a straight-chain $C_1$-$C_4$ - alkyl or cyanoethyl.

The composition according to the present invention is suitable in an advantageous manner for the control of plant pest populations from the insect categories of Lepidoptera and Coleoptera. The composition in accordance with the invention provides its activity particularly with respect to the freshly laid eggs or egg spawns of the insects.

The surprising good nematocidal activity of the composition described above embraces also larvicide and ovicide activities with root gall nematodes as well as an emergence restraining effect with respect to the cyst-forming root nematodes (Meloidogyne - and Heterodera types), whereby they indeed surpass the conventionally known preparations of the same general activity according to vitro results.

It is of particular advantage that the composition according to the present invention can be employed for influencing the onset of any resistance by the harmful organism populations and for modern methods of control.

The application amount is determined according to the type of harmful pests to be controlled and amounts in general to between 0.5 and 20 kg/ha.

Of the compounds characterized by general formula I, those which are distinguished by a particularly good activity have the following substituents:

R is Phenyl, 2-Fluorophenyl, 3-Fluorophenyl, 4-Fluorophenyl, 2-Chlorophenyl, 3-Chlorophenyl, 4-Chlorophenyl, 2-Bromophenyl, 3-Bromophenyl, 4-Bromophenyl, 2-iodophenyl, 3-iodophenyl, 4-iodophenyl, 2,4-Difluorophenyl, 2,6-Difluorophenyl, Pentafluorophenyl, 2,4-Dichlorophenyl, 3,4-Dichlorophenyl, 2-Chloro-6-fluorophenyl, 2-Methylphenyl, 3-Methylphenyl, 4-Methylphenyl, 2-Methoxyphenyl, 3-Methoxyphenyl, 4-Methoxyphenyl, 2-Methylthiophenyl, 3-Methylthiophenyl, 4-Methylthiophenyl, 3-Trifluoromethylphenyl, 4-Trifluoromethylphenyl, 2-Pyridyl, 3-Pyridyl, 4-Pyridyl, 2-Thienyl, 3-Thienyl or 1-Naphthyl and $R_1$ is Methyl, Ethyl, Propyl, Butyl or Cyanoethyl.

A particularly outstanding insecticidal and ovicidal activity is evidenced for example by the following compounds:
α-Methylthio-cinnamic acid nitrile and
α-Methylthio-2-fluorocinnamic acid nitrile.

Mention may be made by way of example of the following particularly nematocidal by effective compounds:
α-Methylthio-4-chlorocinnamic acid nitrile
α-Methylthio-4-bromocinnamic acid nitrile
α-Methylthio-4-fluorocinnamic nitrile.

The compounds to be employed according to the present invention can be used either alone, in mixture with one another or with other active substances. If necessary, other plant protection or pest control agents can be added, indeed according to the desired purpose.

To the extent that a broadening of the activity spectrum is considered, other biocides can also be added. Moreover, even non-phytotoxic agents can be employed which, together with biocides, are able to provide a synergistic increase in activity, such as wetting agents, emulsifiers, solvents and oily additives.

Examples of other additives for inclusion in the composition of the invention are phospholipids, for example those from the groups Phosphatidylcholine, the hydrated Phosphatidylcholines, Phosphatidylethanolamine, the N-Acyl-phosphatidylethanolamines, Phosphatidylinosite, Phosphatidylserine, Lysolecithin and Phosphatidylglycerol.

Advantageously the active substances or their mixtures are employed in the form of preparations such as powders, spray agents, granulates, solutions, emulsions or suspensions, with the addition of liquid and/or solid carrier substances or diluting agents and, if necessary, wetting, adhering, emulsifying and/or dispersing adjuvants.

Suitable liquid carriers include, for example, water, aliphatic and aromatic hydrocarbons, such as Benzene, Toluene, Xylene, Cyclohexanone, Isophorone, Dimethylsulfoxide, moreover Mineral oil fractions and plant oils.

Suitable as solid carrier materials are mineral earths, for example Tonsil, Silicagel, Talcum, Kaolin, Attapulgite, Limestone, Silicic acid and plant derived products, for example, meal.

Surface-active substances that can be employed according to the present invention include, for example, Calcium lignin sulfonate, Polyoxyethylenealkylphenylether, Naphthalene sulfonic acids and their salts, Phenol sulfonic acids and their salts, Formaldehyde condensates, fatty alcohol sulfate as well as substituted benzene sulfonic acids and their salts.

To the extent that the active substances according to the present invention are supposed to be employed for the disinfecting of seeds, even dyes can be admixed in order to provide the disinfected seeds with a clearly visible coloration.

The amount of the active substance(s) in the different preparations can vary within broad limits. For example, a composition may contain about 10 to 90 percent by weight active substance, about 90 to 10 percent by weight liquid or solid carrier material, as well as if necessary up to 20 percent by weight surface-active substance, with corresponding reduction in the amount of carrier material.

The application of the composition can take place in customary manner, for example with water as carrier in sprayable amounts of about 100 up to 1000 liter/ha. Employment of the composition in so-called "low volume" or "ultra-low volume" techniques is likewise possible, as is their application in the form of so-called microgranulates.

The following examples are set forth to illustrate production of the preparations according to the present invention:

A. SPRAY POWDER (a)

40% by weight active substance
25% by weight clay minerals
20% by weight silicic acid
10% by weight cell pitch
5% by weight surface-active substance based upon a mixture of the calcium salt of lignin sulfonic acid with alkylphenolpolyglycolethers (b)

25% by weight active substance
60% by weight kaolin
10% by weight silicic acid
5% by weight surface-active substance based upon the sodium salt of N-methyl-N-oleyl-taurine and the calcium salt of ligninsulfonic acid (c)

10% by weight active substance
60% by weight clay minerals
15% by weight silicic acid
10% by weight cell pitch
5% by weight surface-active substance based upon the sodium salt of N-methyl-N-oleyl-taurine and the calcium salt of ligninsulfonic acid

B. PASTE

45% by weight active substance
5% by weight sodium aluminum silicate
15% by weight Cetylpolyglycolether with 8 Mole ethylene-oxide
2% by weight spindle oil
10% by weight Polyethyleneglycol
23 parts water

C. EMULSION CONCENTRATE

25% by weight active substance
15% by weight Cyclohexanone
55% by weight Xylene
5% by weight mixture of Nonylphenylpolyoxyethylene or Calcium dodecylbenzene sulfonate.

The compounds to be employed according to the present invention can be prepared in particularly advantageous manner by condensing an aromatic aldehyde of the general formula

R—CHO    II with an Alkylthioacetonitrile

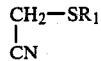

in the presence of 18-crown-6 as catalyst and with the addition of a base, if necessary dissolved in a solvent. Thereafter the desired reaction product is isolated in the known manner.

As a general rule Z E-isomers are produced on account of the double bond. The isomers can be separated, if desired, with the aid of traditional methods, such as fractional distillation or column chromatography. However, according to the present invention it is not only the particular Z-respectively E-components but also the Z, E-isomer mixture than can be employed.

The condensation reaction between aldehyde and alkylthioacetonitrile can be carried out with or without solvents. Suitable as solvents are mainly those substances inert with respect to the reactants, such as alcohols, ether, acetonitrile, toluene among others.

The reaction can be carried out generally within the basic pH-range, whereby alkali hydroxide can be added in small amounts (about 0.1 equivalent) as base, and with catalytic amounts of 18-crown-6.

The $\alpha$-alkylthiocinnamic acid nitriles according to the present invention are generally colorless to yellow colored liquids of ester-like odor. They dissolve well in organic solvents, such as for example Benzene, Xylene, Cyclohexanone, Acetone, Methylenechloride, Chloroform, Ethanol, Acetonitrile and Dimethylformamide. They are less than one percent soluble in water.

The novel features which are considered as chacteristic for the invention are set forth in particular in the appended claims. The invention itself, however, both as to its construction and its method of operation, together with additional objects and advantages thereof, will be best understood from the following description of specific embodiments.

EXAMPLE ONE $\alpha$-Methylthio-2-fluorocinnamic acid nitriles, Isomer mixture 65.36 g (0.75 Mol) Methylthioacetonitrile are dissolved in 750 ml Tetrahydrofuran. Then 5.6 g (0.1 Mol) Potassium hydroxide and 0.3 g 18-Crown-6 are added thereto. At 10° C. and within a period of 20 minutes 93.08 g 2-Fluorobenzaldehyde in 250 ml Tetrahydrofuran are added dropwise. The reaction mixture is then stirred for two hours at 10° C. and allowed to stand overnight. The solution is then filtered and the residue is washed with Tetrahydrofuran. It is then rotated in a vacuum, the remaining oil is withdrawn in one liter ethyl acetate and washed two times, each with 500 ml dilute sodium chloride solution. The ethyl acetate phase is dried over magnesium sulphate and after filtering off it is rotated in a vacuum. Subsequently the residue is distilled in an oil pump vacuum.

$K_{P0.1-0.2}$:98°–103° C. $n_D^{20}$:1.6155.
Yield: 105.1 g=72.5% of Theoretical
A 60:40 E, Z-mixture is provided.

EXAMPLE TWO

Separation of Z, E-α-Methylthio-2-fluorocinnamic acid nitrile into E-α-Methylthio-2-fluorocinnamic acid nitrile and Z-α-Methylthio-2-fluorocinnamic acid nitrile Preparative HPOC-chromatography of 210 mg Z, E-α-Methylthio-2-fluorocinnamic acid nitrile with isooctane: diisopropylether = 1,000 ml: 4 ml provides: 115 mg E-α-Methylthio-2-fluorocinnamic acid nitrile

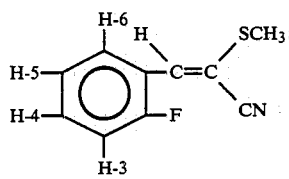

1H-NMR: $SCH_3$: 2.5 ppm(s); H-3, H-4, H-5, H C=: 6.9–7.5 ppm(m); H-6 : 8.03 ppm(m) and 84 mg Z-α-Methylthio-2-Fluorocinnamic acid nitrile

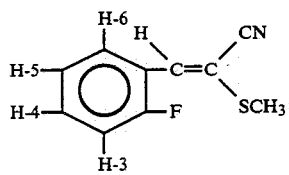

1H-NMR: $SCH_3$: 2.57 ppm(s); H-3, H-4, H-5, H C=: 6.9–7.5 ppm(m); H-6 : 7.78 ppm(m)

In a manner analogous to that set out in Example One, the following compounds have been prepared according to the present invention:

| Example No. | Name of Compound | Physical Constant |
|---|---|---|
| 3 | α-Ethylthio-cinnamic acid nitrile, Isomer mixture | Kp 136–42° C./0.4 mm |
| 4 | α-Ethylthio-2-chlorocinnamic acid nitrile, Isomer mixture | Kp 155–57° C./1 mm |
| 5 | α-Ethylthio-4-chlorocinnamic acid nitrile, Isomer mixture | Kp 130–35° C./0.05 mm |
| 6 | α-Ethylthio-2,4-dichlorocinnamic acid nitrile, Isomer mixture | Kp 125–30° C./0.05 mm |
| 7 | α-Ethylthio-3,4-dichlorocinnamic acid nitrile, Isomer mixture | Kp 142–48° C./0.05 mm |
| 8 | 2-Ethylthio-3-(pyridine-2-yl)-acylnitrile, Isomer mixture | Kp 145–50° C./0.05 mm |
| 9 | 2-Ethylthio-3-(2-thienyl)-acrylonitrile, Isomer mixture | Kp 118–25° C./0.05 mm |
| 10 | α-Ethylthio-2-methylcinnamic acid nitrile, Isomer mixture | Kp 115–22° C./0.05 mm |
| 11 | α-Ethylthio-3-chlorocinnamic acid nitrile, Isomer mixture | Kp 125–30° C./0.05 mm |
| 12 | α-Methylthio-cinnamic acid nitrile, Isomer mixture | Kp 130–32° C./0.4 mm |
| 13 | α-Methylthio-3-chlorocinnamic acid nitrile, Isomer mixture | Kp 128–30° C./0.05 mm |
| 14 | α-Methylthio-2-methylcinnamic acid nitrile, Isomer mixture | Kp 115–19° C./0.05 mm |
| 15 | α-Methylthio-4-cinnamic acid nitrile, Isomer mixture | $n_D^{20}$: 1.6575 |
| 16 | α-Methylthio-2-chlorocinnamic acid nitrile, Isomer mixture | $n_D^{20}$: 1.6401 |
| 17 | α-Methylthio-4-bromocinnamic acid nitrile, Isomer mixture | $n_D^{20}$: 1.6780 |
| 18 | α-Methylthio-2-methoxycinnamic acid nitrile, Isomer mixture | $n_D^{20}$: 1.6365 |
| 19 | α-Methylthio-4-fluorocinnamic acid nitrile, Isomer mixture | $n_D^{20}$: 1.6165 |
| 20 | 2-Methylthio-3-(1-naphthyl)-acrylonitrile, Isomer mixture | $n_D^{20}$: 1.6950 |
| 21 | 2-Methylthio-3-(3-pyridyl)-acrylonitrile, Isomer mixture | $n_D^{20}$: 1.6405 |
| 22 | 2-Methylthio-3-(2-pyridyl)-acrylonitrile, Isomer mixture | $n_D^{20}$: 1.6240 |
| 23 | α-Methylthio-2,4-dichlorocinnamic acid nitrile, Isomer mixture | MP: 65–66° C. |
| 24 | α-Methylthio-3-trifluorocinnamic acid nitrile, Isomer mixture | $n_D^{20}$: 1.5575 |
| 25 | 2-chloro-6-fluoro-α-methylthio cinnamic acid nitrile | $n_D^{20}$: 1.6020 |
| 26 | α-Methylthio-4-trifluoromethylcinnamic acid nitrile, Isomer mixture | $n_D^{20}$: 1.5655 |
| 27 | α-Ethylthio-2-fluorocinnamic acid nitrile, Isomer mixture | $n_D^{20}$: 1.6020 |
| 28 | α-Methylthio-4-methylcinnamic acid nitrile, Isomer mixture | $n_D^{20}$: 1.6345 |

The following operational examples serve to illustrate various use possibilities of the composition according to the present invention and which follow in the form of the above set forth preparations.

EXAMPLE TWENTY-NINE

Ovicidal activity with egg spawn of the Egyptian cotton moth (*Spodoptera littoralis*)

The compounds to be used according to the present invention are employed as aqueous suspensions with an active substance concentration of 0.1 percent. Into this active substance preparation there are immersed one day old egg spawns, which have been deposited onto filter paper from fertilized female moths, until complete wetting thereof. These are then placed for four days in closed Petri dishes for purposes of evaluation. Criteria for the activity valuation is the percentage of avoidance of the appearance of moths in comparison to the untreated egg spawns.

The obtained results are set forth and summerized in the following table:

| Compounds | Active Subtance Concentration in % | Avoidance of Appearance of Moths in % |
|---|---|---|
| α-Ethylthio-cinnamic acid nitrile, Isomer mixture | 0.1 | 100 |
| α-Ethylthio-2-chlorocinnamic acid nitrile, Isomer mixture | 0.1 | 100 |
| α-Ethylthio-4-chlorocinnamic acid nitrile, Isomer mixture | 0.1 | 100 |
| α-Ethylthio-2,4-dichlorocinnamic acid nitrile, Isomer mixture | 0.1 | 100 |
| α-Ethylthio-3,4-dichlorocinnamic acid nitrile, Isomer mixture | 0.1 | 100 |
| 2-Ethylthio-3-(pyridine-2-yl)-acylnitrile, Isomer mixture | 0.1 | 100 |
| 2-Ethylthio-3-(2-thienyl)-acrylnitrile, Isomer mixture | 0.1 | 100 |
| α-Ethylthio-2-methylcinnamic acid nitrile, Isomer mixture | 0.1 | 100 |
| α-Ethylthio-3-chlorocinnamic acid nitrile, Isomer mixture | 0.1 | 100 |

-continued

| Compounds | Active Subtance Concentration in % | Avoidance of Appearance of Moths in % |
|---|---|---|
| α-Methylthiocinnamic acid nitrile, Isomer mixture | 0.1 | 100 |
| α-Methylthio-3-chlorocinnamic acid nitrile, Isomer mixture | 0.1 | 100 |
| α-Methylthio-2-methylcinnamic acid nitrile, Isomer mixture | 0.1 | 100 |
| α-Methylthio-4-cinnamic acid nitrile, Isomer mixture | 0.1 | 100 |
| α-Methylthio-2-chlorocinnamic acid nitrile, Isomer mixture | 0.1 | 100 |
| α-Methylthio-4-bromocinnamic acid nitrile, Isomer mixture | 0.1 | 100 |
| α-Methylthio-2-fluorocinnamic acid nitrile, Isomer mixture | 0.1 | 100 |
| α-Methylthio-2-methoxycinnamic acid nitrile, Isomer mixture | 0.1 | 100 |
| α-Methylthio-4-fluorocinnamic acid nitrile, Isomer mixture | 0.1 | 100 |
| 2-Methylthio-3-(1-naphthyl)-acrylonitrile, Isomer mixture | 0.1 | 100 |
| 2-Methylthio-3-(3-pyridyl)-acrylonitrile, Isomer mixture | 0.1 | 100 |
| α-Methylthio-2,4-dichloro-cinnamic acid nitrile, Isomer mixture | 0.1 | 100 |
| α-Methylthio-3-trifluoromethyl cinnamic acid nitrile, Isomer mixture | 0.1 | 100 |
| 2-Chlor-6-fluoro-α-methyl-thio-cinnamic acid nitrile | 0.1 | 100 |
| α-Methylthio-4-trifluoromethylcinnamic acid nitrile, Isomer mixture | 0.1 | 100 |
| α-Ethylthio-2-fluorocinnamic acid nitrile, Isomer mixture | 0.1 | 100 |
| E—α-Methylthio-2-fluoro-cinnamic acid nitrile | 0.1 | 100 |
| Z—α-Methylthio-2-fluoro-cinnamic acid nitrile | 0.1 | 100 |
| α-Methylthio-4-methylcinnamic acid nitrile, Isomer mixture | 0.1 | 100 |

EXAMPLE THIRTY

Ovicidal activity with egg spawn of the Egyptian cotton moth (*Spodoptera littoralis*)

The compounds to be employed according to the present invention, as well as the comparison substances, are used as aqueous suspensions respectively emulsions having the desired concentrations. Into this active substance preparation are immersed one day old egg spawns, which have been deposited onto filter paper from fertilized female moths, until complete wetting thereof. The same are then placed for four days in closed Petri dishes for purposes of evaluation. Criteria for the activity evaluation is the percentage of avoidance of the appearance of moths in comparison to the untreated egg spawns.

The obtained results are set forth and summarized in the following table:

| Compounds | Active Substance Concentration in % | Avoidance of Appearance of Moth in % |
|---|---|---|
| α-Methylthio-cinnamic acid nitrile | 0.0064 | 100 |
| α-Methylthio-2-fluoro-cinnamic acid nitrile | 0.0064 | 95 |
| Comparison Agent according to | | |
| U.S. Pat. No. 3828091 | | |
| 2-(4-Chlorophenyl)-3-iso-propylthio-acrylonitrile | 0.0064 | 0 |
| 2-3-Butylthio-2-(4-Chloro-phenyl)-acrylonitrile | 0.0064 | 0 |
| 2-(4-Chlorophenyl)-3-ethyl-thio-acrylonitrile | 0.0064 | 0 |

EXAMPLE THIRTY-ONE

Ovicidal activity with egg spawns of the Mexican bean beetle (*Epilachna varivestis*)

The compounds to be used according to the present invention, as well as the comparison substances, are employed as aqueous suspensions respectively emulsions with having the desired concentrations. Into this active substance preparation are immersed one day old egg spawns, which have been deposited from fertilized female beetles onto primary leaves of the bush bean (*Phaseolus vulgaris*), until complete wetting. They are then deposited and kept for six days in closed Petri dishes. Criteria for the evaluation of activity is the percentage of avoidance of the appearance of moths in comparison to the untreated egg spawns.

The obtained results are set forth and summarized in the following table:

| Compounds | Active Substance Concentration in % | Avoidance of Appearance of Moths in % |
|---|---|---|
| α-Methylthio-cinnamic acid nitrile | 0.04 | 95 |
| α-Methylthio-2-fluorocinnamic acid nitrile | 0.04 | 95 |
| αEthylthio-2-fluorocinnamic acid nitrile | 0.04 | 50 |
| Comparison Agent According to U.S. Pat. No. 3 828 091 | | |
| 2-(4-Chlorophenyl)-3-Isopropyl-thioacrylonitrile | 0.04 | 0 |
| 2-3-Butylthio-2-(4-chlorophenyl)-acrylonitrile | 0.04 | 0 |
| 2-(4-Chlorophenyl)-3-ethyl-thioacrylonitrile | 0.04 | 0 |

EXAMPLE THIRTY-TWO

Nematocidal effectiveness with L₂-larvae of the root gall nemotode (*Meloidogyne incognita*).

The compounds to be employed according to the present invention are prepared as suspensions of powder form formulations: the comparison agents are provided as aqueous solution. Freshly evolved $L_2$-larvae from egg spawns of root gall nemotodes are placed in the solutions and after 24 hours the activity respectively inactivity of the larvae are determined by microscopy. The results are set forth in the following table.

| Compounds | Active Substance Concentration | | | | |
|---|---|---|---|---|---|
| | 0.01 | 0.005 | 0.0025 | 0.0012 | 0.0006% |
| α-Methylthio-4-chloro-cinnamic acid nitrile | 100 | 100 | 100 | 100 | 100% |

-continued

| Compounds | Active Substance Concentration | | | | |
|---|---|---|---|---|---|
| | 0.01 | 0.005 | 0.0025 | 0.0012 | 0.0006% |
| α-Methylthio-4-bromocinnamic acid nitrile | 100 | 100 | 100 | 100 | 100% |
| α-Methylthio-4-fluorocinnamic acid nitrile | 100 | 100 | 100 | 100 | 95% |
| Comparison Agent | | | | | |
| 1-(Dimethylaminocarbonyl)-N—(methylaminocarbonyloxy)-thioformhydroxamic acid-methyl-ester | 100 | 95 | 70 | 30 | 0% |
| Untreated Control | 0 | 0 | 0 | 0 | 0% |

EXAMPLE THIRTY-THREE

Ovicidal effectiveness with egg spawns of root gall nemotode (*Meloidogyne incognita*)

The compounds to be employed according to the present invention are prepared as a suspension of a powder form formulation, whereas the comparison agents are provided as aqueous solution. Freshly obtained egg spawns from *Capsicum anuum* are washed and then placed into the solution. After a period of 48 hours there is carried out a substantial washing of the treated egg spawns under flowing water. For each of the concentrations five egg spawns are put into clear water and allowed to develop at a temperature of 24° C. until the emergence of larvae. The following table shows the number of appearing $L_2$-larvae from each five egg spawns after eight days.

| Compounds | Active Substance Concentration | | | |
|---|---|---|---|---|
| | 0.01 | 0.005 | 0.0025 | 0.0012% |
| α-Methylthio-4-chlorocinnamic acid nitrile | 0 | 0 | 0 | 0 |
| α-Methylthio-4-bromocinnamic acid nitrile | 0 | 0 | 0 | 0 |
| α-Methylthio-4-fluorocinnamic acid nitrile | 0 | 0 | 0 | 50 |
| Comparison Agent | | | | |
| 1-(Dimethylaminocarbonyl)-N—(methylaminocarbonyloxy)-thioformhydroxamic acid-methyl-ester | 400 | 400 | 400 | 400 (app.) |
| Untreated Control | 400 | 400 | 400 | 400 (app.) |

EXAMPLE THIRTY-FOUR

The Emergence-restraint activity regarding the cyst content of *Heterodera schachtii*

The compounds to be employed according to the present invention are prepared as suspension of powder form formulations: the comparison agents are presented as aqueous solution. Cysts of the rape nematode *Heterodera schachtii* are thoroughly washed under flowing water after a working period of 48 hours, and are placed into root diffusate at 24° C. for purposes of $L_2$-larvae emergence, five cysts for each concentration.

The following table shows the number of emergent $L_2$-larvae from each five cysts after eight days.

| Compounds | Active Substance Concentration: | | | |
|---|---|---|---|---|
| | 0.02 | 0.01 | 0.005 | 0.0025% |
| α-Methylthio-4-chlorocinnamic acid nitrile | 0 | 0 | 0 | 0 |
| Comparison Agent | | | | |
| 1-(Dimethylaminocarbonyl)-N—(methylaminocarbonyloxy)-thioformhydroxamic acid-methyl-ester | 400 | 400 | 400 | 400 |
| Untreated Control | 400 | 400 | 400 | 400 |

Although the invention has been described as embodied in α-alkylthiocinnamic acid nitriles for the control of harmful organisms, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential chacteristics of the generic or specific aspects of this invention.

We claim:

1. Method for controlling insects and nematodes as well as their larvae and eggs, comprising applying onto or about the locus of said insects, nematodes, larvae or eggs an effective amount of a composition comprising at least one α-alkylthiocinnamic acid nitrile of the formula

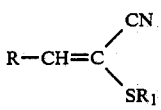

I wherein
R is an aromatic hydrocarbon or an aromatic hydrocarbon substituted one or more times, the same or differently, by halogen, $C_1$–$C_4$-alkyl, $C_1$–$C_4$-alkoxy, $C_1$–$C_4$-alkylthio or trifluoromethyl and
$R_1$ is a straight-chain $C_1$–$C_4$-alkyl or cyanoethyl in admixture with a suitable carrier.

2. Method according to claim 1 wherein said composition is applied in an amount between 0.5 and 200 hg/ha.

* * * * *